(12) United States Patent
Ferrari et al.

(10) Patent No.: US 8,282,654 B2
(45) Date of Patent: Oct. 9, 2012

(54) CLIP AND CLIP APPLICATOR FOR CLOSING BLOOD VESSELS

(75) Inventors: Mauro Ferrari, Pisa (IT); Cesare Stefanini, Pisa (IT)

(73) Assignee: Karl Storz GmbH & Co. KG (DE)

( * ) Notice: Subject to any disclaimer, the term of this patent is extended or adjusted under 35 U.S.C. 154(b) by 950 days.

(21) Appl. No.: 11/291,722

(22) Filed: Dec. 1, 2005

(65) Prior Publication Data

US 2006/0271103 A1 Nov. 30, 2006

(30) Foreign Application Priority Data

May 31, 2005 (DE) .................... 20 2005 009 061 U

(51) Int. Cl.
*A61B 17/00* (2006.01)
(52) U.S. Cl. ........................................ 606/142; 606/139
(58) Field of Classification Search .................. 606/158, 606/151, 213, 139, 142, 157, 143, 152, 153, 606/215, 216, 219, 220; 378/180; 227/176.1, 227/175.1–182.1, 19; 29/513; 411/920
See application file for complete search history.

(56) References Cited

U.S. PATENT DOCUMENTS

| | | | | |
|---|---|---|---|---|
| 320,451 A * | 6/1885 | Walter | ............................ | 24/94 |
| 1,756,385 A * | 4/1930 | Rau | ................................ | 411/461 |
| 2,309,536 A * | 1/1943 | Reid et al. | ..................... | 411/473 |
| 2,323,362 A * | 7/1943 | Weiss | ............................ | 174/159 |
| 2,887,004 A * | 5/1959 | Stewart | ......................... | 411/470 |
| 2,964,751 A * | 12/1960 | Lang | ............................ | 29/432.1 |
| 3,889,338 A * | 6/1975 | Hosaka | ....................... | 29/243.56 |
| 4,789,090 A * | 12/1988 | Blake, III | ........................ | 227/19 |
| 4,887,601 A * | 12/1989 | Richards | ....................... | 606/219 |
| 4,934,364 A * | 6/1990 | Green | ............................ | 606/143 |
| 5,154,189 A * | 10/1992 | Oberlander | ................... | 128/898 |
| 5,158,567 A * | 10/1992 | Green | ............................ | 606/219 |
| 5,236,440 A * | 8/1993 | Hlavacek | ....................... | 606/219 |
| 5,246,443 A * | 9/1993 | Mai | .................................. | 606/78 |
| 5,297,714 A * | 3/1994 | Kramer | ....................... | 227/175.1 |
| 5,350,400 A * | 9/1994 | Esposito et al. | .............. | 606/219 |
| 5,389,098 A * | 2/1995 | Tsuruta et al. | .................. | 606/41 |
| 5,439,479 A * | 8/1995 | Shichman et al. | ............. | 606/220 |
| 5,478,354 A * | 12/1995 | Tovey et al. | ..................... | 606/219 |
| 5,560,532 A * | 10/1996 | DeFonzo et al. | ............ | 227/176.1 |
| 5,582,611 A * | 12/1996 | Tsuruta et al. | .................. | 606/46 |
| 5,695,504 A * | 12/1997 | Gifford et al. | ................. | 606/153 |
| 5,725,537 A * | 3/1998 | Green et al. | ..................... | 606/143 |
| 5,749,896 A * | 5/1998 | Cook | ............................. | 606/219 |
| 5,779,720 A * | 7/1998 | Walder-Utz et al. | .......... | 606/151 |
| 5,810,846 A * | 9/1998 | Virnich et al. | ................. | 606/142 |
| 5,976,159 A * | 11/1999 | Bolduc et al. | .................. | 606/142 |
| 6,197,042 B1 * | 3/2001 | Ginn et al. | ..................... | 606/213 |
| 6,277,131 B1 * | 8/2001 | Kalikow | ......................... | 606/143 |
| 6,582,452 B2 * | 6/2003 | Coleman et al. | .............. | 606/213 |
| 6,623,510 B2 * | 9/2003 | Carley et al. | .................. | 606/213 |

(Continued)

*Primary Examiner* — Gary Jackson
*Assistant Examiner* — Erin Colello
(74) *Attorney, Agent, or Firm* — St. Onge Steward Johnston & Reens LLC

(57) ABSTRACT

A clip for closing blood vessels which branch off from a main blood vessel during an intervention of the main blood vessel has a base body via which the clip can be placed on an inside face of the opened main blood vessel. At least three limbs protrude from the base body and are able to be bent in the direction towards the base body in order to clamp tissue in the area of the branch between the base body and the bent-back limbs thereby closing said branch.

2 Claims, 5 Drawing Sheets

U.S. PATENT DOCUMENTS

| | | | |
|---|---|---|---|
| 6,629,988 B2 * | 10/2003 | Weadock | 606/219 |
| 6,640,399 B2 * | 11/2003 | Perez Romo | 24/570 |
| 6,679,894 B2 * | 1/2004 | Damarati | 606/143 |
| 6,767,356 B2 * | 7/2004 | Kanner et al. | 606/213 |
| 7,094,244 B2 * | 8/2006 | Schreck | 606/139 |
| 7,228,999 B2 * | 6/2007 | Oide et al. | 227/155 |
| 7,267,682 B1 * | 9/2007 | Bender et al. | 606/219 |
| 7,311,236 B2 * | 12/2007 | Smith et al. | 227/131 |
| 2002/0190093 A1 * | 12/2002 | Fenton, Jr. | 227/176.1 |
| 2004/0010272 A1 * | 1/2004 | Manetakis et al. | 606/143 |
| 2007/0034666 A1 * | 2/2007 | Holsten et al. | 227/176.1 |
| 2007/0198058 A1 * | 8/2007 | Gelbart et al. | 606/213 |

\* cited by examiner

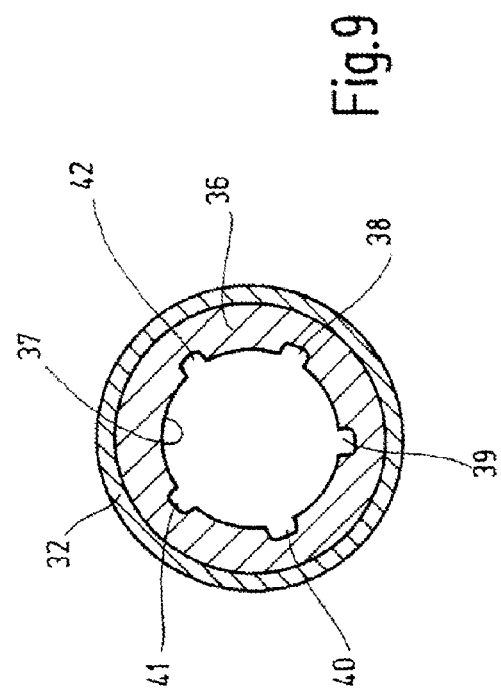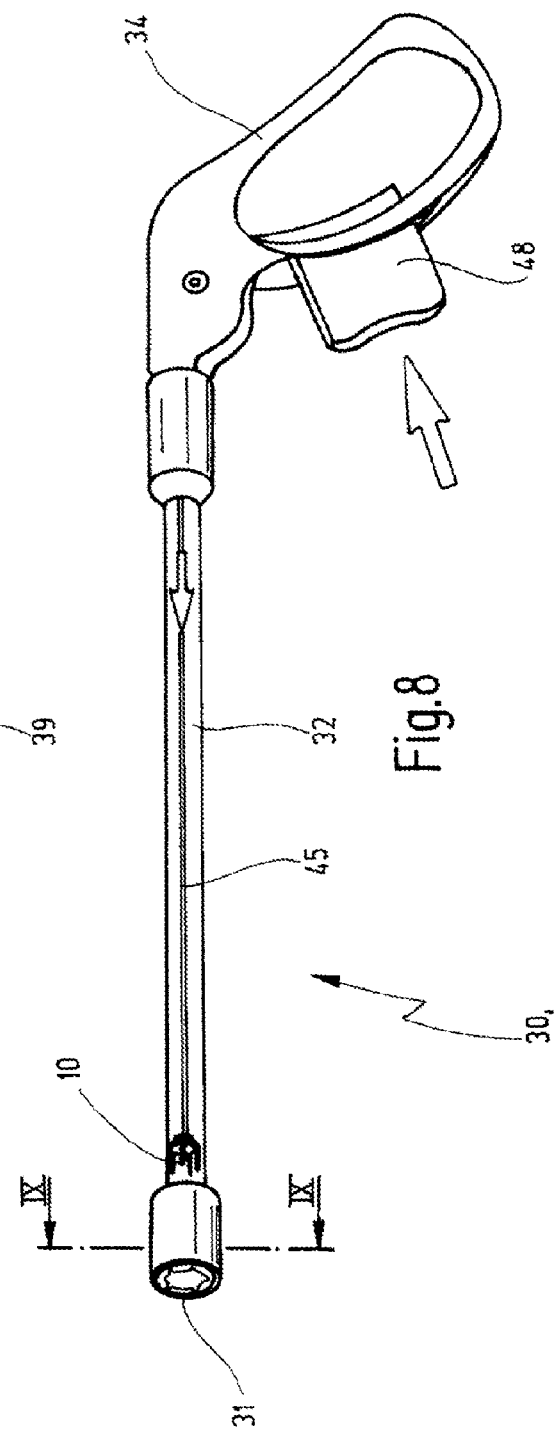

CLIP AND CLIP APPLICATOR FOR CLOSING BLOOD VESSELS

CROSS-REFERENCE TO RELATED APPLICATIONS

This application claims priority of German Patent Application No. 20 2005 009 061.1 filed on May 31, 2005.

FIELD OF THE INVENTION

The invention relates to a clip for closing blood vessels, which branch off from a main blood vessel, for example from the aorta, during an intervention on the main blood vessel.

The invention relates likewise to a clip applicator for applying a clip of this kind.

BACKGROUND OF THE INVENTION

Clips are used in the medical sector for clamping blood vessels during surgery. The clips are usually U-shaped or V-shaped and are made from a wire-shaped material. By means of the clip applicator, the clips are applied laterally to the blood vessel that is to be closed, and the two free ends are bent towards one another, as a result of which the vessel lying between them is clamped such that there can be no more flow of blood.

In a particular surgical technique for repairing of blood vessels, a stent is inserted into a blood vessel, in most cases a main blood vessel, for example the aorta. To do so, the corresponding section of the aorta has to be clamped off from the blood flow in order to insert the stent. To do this, the aorta is cut open along its length in the clamped-off region.

After the stent has been inserted and sutured to the aorta, the clamping on both sides is removed again.

When the aorta is clamped off, blood flows back to organs via blood vessels branching off from the main blood vessel, for example via the arteries. Branching-off blood vessels of this kind in most cases have a diameter of 2 to 3 mm, and approximately six to eight such branching-off blood vessels are present in the region of the aorta.

Such a return flow has to be prevented, however. To do so, the corresponding organ or vessel has hitherto been closed by hand.

It is therefore an object of the invention to provide a clip which, during an surgery on a main blood vessel, permits closure of blood vessels that branch off from this main blood vessel.

It is an further object of the invention to provide a clip applicator for applying such a clip.

SUMMARY OF THE INVENTION

According to one aspect of the invention, the object is achieved by a clip having a base body via which the clip can be placed on an inside face of the opened main blood vessel, and at least three limbs are provided which protrude from the base body and are able to be bent in a direction towards the base body in order to clamp tissue, in the area of the branch, between base body and bent-back limbs, by which means this branch is closed.

According to an other aspect of the invention, the object is achieved by a clip applicator having a housing for receiving at least one clip, with an advancer mechanism for pushing a clip forwards, and with a deflector element for bending back the limbs of a clip that has been pushed forwards and has struck the deflector element.

By provision of the base body, the clip can be applied to the inside face of the main blood vessel in the area where one or more further blood vessels to be closed branch off. By provision of the several, i.e. at least three, limbs that can be bent back, tissue of the main vessel can be pinched between the base body and the bent-back limbs, and the branch can be closed in this way. The pinched tissue "plugs" the branch opening of the branching-off blood vessel. In this way, the undesired return flow to the organs supplied by these further blood vessels can then be interrupted during the actual operation on the aorta. The branching blood vessels can be closed temporarily or permanently. For removing the clip it is possible to cut it away together with the tissue captured therein or one bend the limbs outwardly for releasing the tissue.

In a further embodiment of the invention, four to six limbs are provided. Preferably five protruding limbs are provided.

Tests have shown that, with a number of limbs in the range of three to six, all the blood vessels branching off in the area of the clip can be closed in one procedure.

In a further embodiment of the invention, the base body has a planar configuration.

This measure has the advantage that the base body can be placed in a planar contact onto an area of the inside face of the opened aorta where the blood vessels branch off. That is to say it can be applied with correct positioning, after which the blood vessels branching off in this area are clamped off by means of the several limbs being bent back. The pinched tissue forms a kind of plug by means of which the branch is sealed off.

In a further embodiment of the invention, the limbs are designed as planar strips.

This measure has the advantage that the pinched tissue will be held gently by the planar strips, and there is no danger of a relatively thin blood vessel of this kind being punctured by a limb.

In a further embodiment of the invention, the base body is disc-shaped.

This measure has the advantage that a cage or pot-shaped structure is obtained with the clip. The clip can be placed from one side onto the main vessel the limbs facing the branch area. Subsequently the branching-off vessels can be closed by the limbs being bent back.

In a further embodiment of the invention, the limbs are bent approximately 90° from the plane of the base body.

In its original form, the clip can be produced such that the base body and the limbs initially extend in one plane, for example by punching or by laser-cutting from a planar base body, after which the limbs are bent away from the base body by 90°.

In the case of a disc-shaped base body, a corresponding clip can then, for example, be inserted simply into a tubular body or into a tubular magazine of the clip applicator, such that handling is simplified.

In a further embodiment of the invention, the clip is produced from metal, in particular from titanium.

This measure has the advantage that materials suitable for the medical sector can be chosen which also have the required mechanical stability to exert the clamping forces.

In a further embodiment of the invention, the length of the limbs is in the range of between the radius and the diameter of the disc-shaped base body of the clip.

This measure has the advantage that the bent-back limbs overlap one another to a greater or lesser extent depending on their length, with the result that the blood vessels are tightly closed by the tissue held between base body and bent-back limbs, and the applied clip sits correspondingly securely in this area.

In a further embodiment of the invention, at least the base body of the clip is coated with polytetrafluoroethylene (PTFE).

This measure has the advantage that any bleeding that occurs can be rapidly eliminated or can be prevented by means of PTFE assisting in the clotting process.

In a further embodiment of the invention, the limbs are pointed at their free ends.

This measure has the advantage that the pointed ends penetrate into the tissue (without cutting or damaging it), and, as they are bent further back, they carry these gripped areas of tissue with them and pinch said areas of tissue between base body and bent-back limbs. This can be likened to the closing of a claw-like excavator shovel.

The clip applicator according to the invention has a housing for receiving at least one clip, an advancer mechanism for pushing a clip forwards, and a deflector element for bending back the limbs of a clip that has been pushed forwards and has struck the deflector element. By means of this design, the clip can be brought up to the main vessel and the limbs can then be bent back in order to close the vessels, by means of the clip being pushed onto the deflector element by the advancer mechanism.

In one embodiment of the clip applicator, the deflector element has oblique deflector surfaces which deflect the limbs of the clip radially inwards.

This measure has the advantage that the operating surgeon can first place the clip applicator correctly in position onto the main vessel. In doing so, he can ensure that the laterally branching-off blood vessels are surrounded by the as yet unbent limbs. When the clip is pushed forwards, these clips are then bent back and close these branching-off blood vessels.

In a further embodiment of the invention, the deflector surfaces begin at different height levels, so that the several limbs can be bent back beginning one after another.

This measure has the advantage that the large number of limbs are bent back in a predetermined sequence, so as to prevent the limbs from becoming entangled with one another as they are bent back. Putting it another way, the limbs are placed over one another, or bent back so as to cross one another, in a very specific pattern.

It will be appreciated that the features mentioned above and those still to be explained below can be used not only in the cited combinations, but also in other combinations or singly, without departing from the scope of the present invention.

BRIEF DESCRIPTION OF THE DRAWINGS

FIG. 1 is The invention is described and explained in more detail below on the basis of a selected illustrative embodiment and with reference to the attached drawings, in which:

FIG. 1 shows a plan view of a clip after the original production process, in which the base body and five limbs extend in one plane, FIG. 8 shows a highly schematic perspective view of a clip applicator according to the invention, FIG. 9 shows a cross section along the line IX-IX in FIG. 8 in the area of the deflector element.

DETAILED DESCRIPTION OF THE INVENTION

A clip shown in the figures is designated overall by reference number 10.

Figure 1:
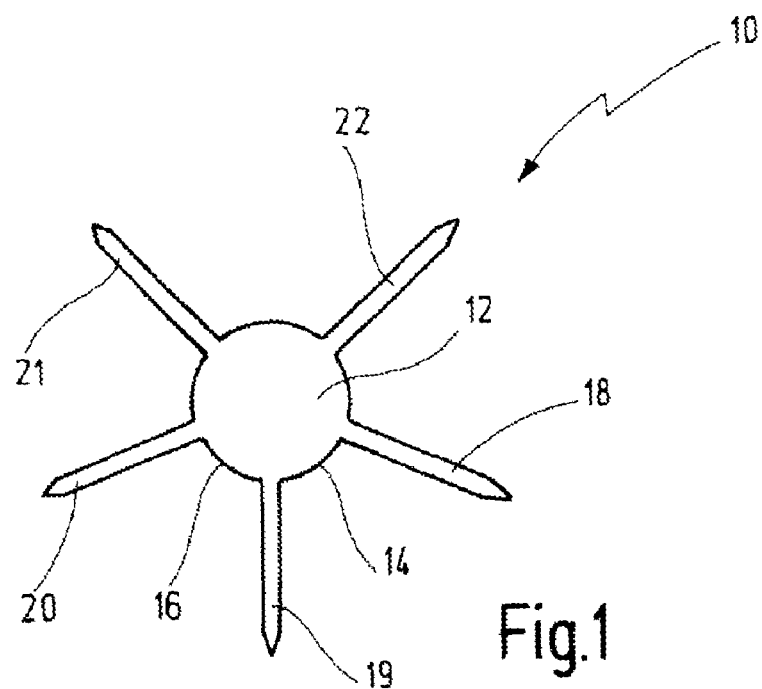

It will be seen from FIG. 1 that a clip 10 has a base body 12 in the form of a disc 14 from whose circumferential edge 16 five limbs 18, 19, 20, 21 and 22 extend.

In its original form, the clip 10 is manufactured such that the disc 14 and limbs 18-22 extend in one plane. This can be done by a punching method or laser-milling or such like.

The length of the limbs 18-22 corresponds approximately to the diameter of the disc 14, and their free end is in each case pointed.

The clip 10 is preferably made of metal, in particular of titanium. The metal body can then be covered over by coating it with polytetrafluoroethylene (PTFE).

Figure 2:
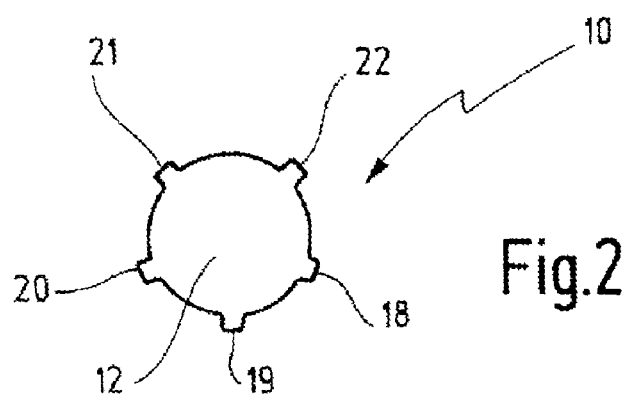
FIG. 2 shows the clip from FIG. 1 after the five limbs have been bent 90° from the plane of the base body in one direction.
Figure 3:
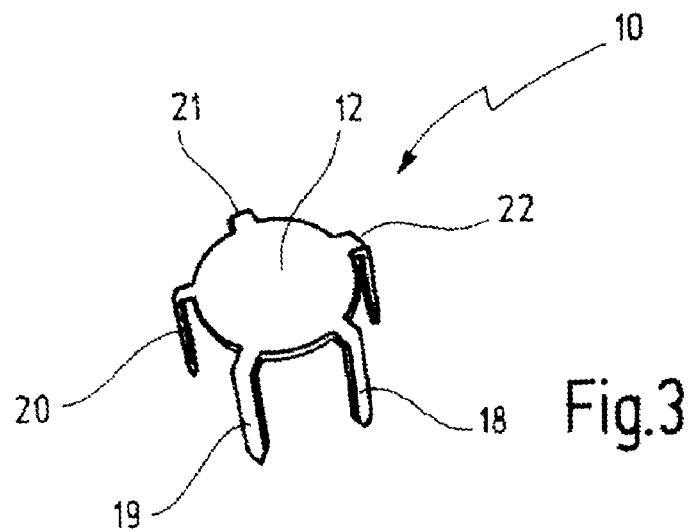
FIG. 3 shows a perspective view of the clip from FIG. 2.

It will be seen from FIGS. 1-3 that each limb 18-22 is designed as a planar, strip-shaped and pointed body. The length of the limb 18-22 can be in the range of several millimeters to a few centimeters, the thickness being in the range of 0.2 to 0.5 mm.

The sequence of views from FIG. 4 to FIG. 7 provides a highly schematic representation of how a clip 10 moves through a deflector element 36 at a distal end 31 of a clip applicator 30 shown in FIGS. 8 and 9 and how the limbs are bent back in this process.

The clip applicator 30 for this purpose has a tubular or shaft-shaped housing 32 in which one clip 10 or if appropriate several clips 10 can be fitted. At the proximal end, a grip 34 having a push button 48 is provided via which a clip 10 can be pushed forward, as is described further below.

The distal end 31 of the housing 32 is provided with the deflector element 36 which is made up of a ring 37 in which five deflector surfaces 38, 39, 40, 41 and 42 are cut which slope radially inwards in the direction from proximal to distal. For pushing the clip 10 forward, the housing 32 contains a rod-shaped advancer mechanism 45 which, when the button 48 is pressed in, moves from proximal to distal and in so doing moves the clip 10 accommodated inside in the distal direction towards the deflector element 36.

Figure 4:
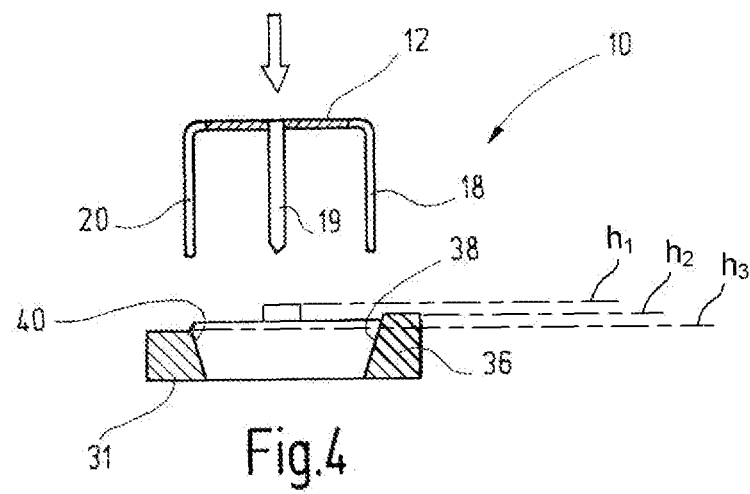
FIG. 4 shows a highly schematic and partially sectioned side view of a clip being moved towards a deflector element of the clip applicator.

FIG. 4 shows a situation in which the limbs 18 and 20 of the clip 10 are in a position shortly before striking the corresponding deflector surfaces 38 and 40. In the cross-sectional view, the deflector surface for the limb 19 cannot be seen, and the two other limbs 21 and 22 are concealed by the limbs 18 and 20.

Figure 5:
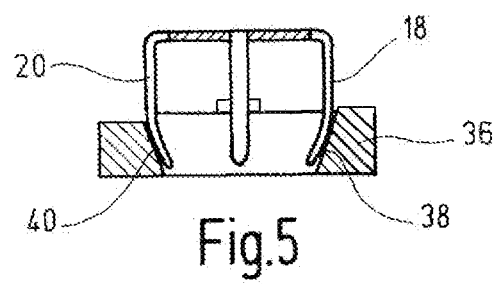
FIG. 5 shows a view corresponding to FIG. 4, with the limbs just beginning to be bent back.

FIG. 5 shows a situation in which the limb 18 has already been bent slightly inwards by the oblique deflector surface 38. The same applies to the limb 20.

Figure 6:
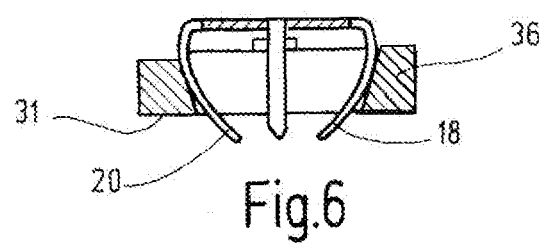
FIG. 6 shows a view comparable to the view in FIG. 5 after further advance of the clip and, accordingly, after further bending back of the limbs, the latter now extending past the distal end of the clip applicator.

When they have been advanced further, as is shown in FIG. 6, the bent-back limbs 18 and 20 protrude past the distal end 31 of the clip applicator 30, and the five limbs 18-22 lie crosswise over one another and form a kind of basket. To ensure that the limbs do not become entangled, the height level of the deflector surfaces 38-42 differs such that the limbs are bent back one after the other and in a particular sequence.

Figure 7:
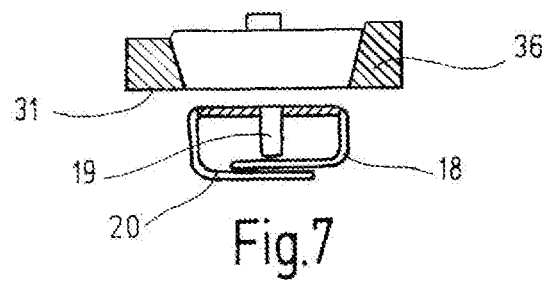
FIG. 7 shows a view corresponding to FIG. 6, after the clip has been pushed completely through the deflector element, with the limbs now completely bent back.

FIG. 7 shows a situation in which the clip 10 is now completely pushed out from the clip applicator 30.

It will be seen that the limb 19 has first been bent back, after which the limb 18 has been placed over the latter, and the limb 20 has in turn been placed over the limb 18. The limbs 19 and 21 are then bent back in a corresponding pattern.

Figure 10:
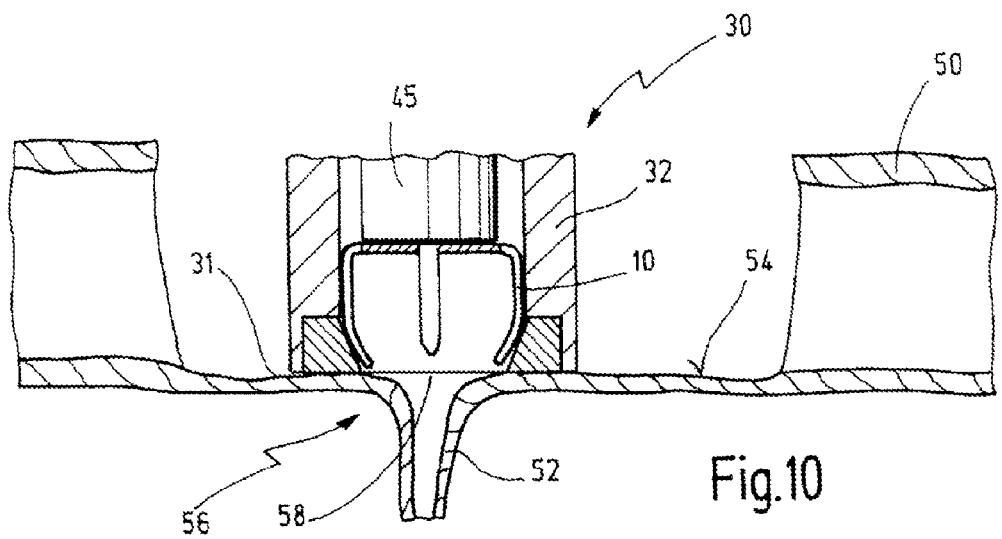
FIG. 10 shows a view comparable to the view in FIG. 5, with the clip applicator placed on an inside face of an aorta in the area where an artery branches off.
Figure 11:
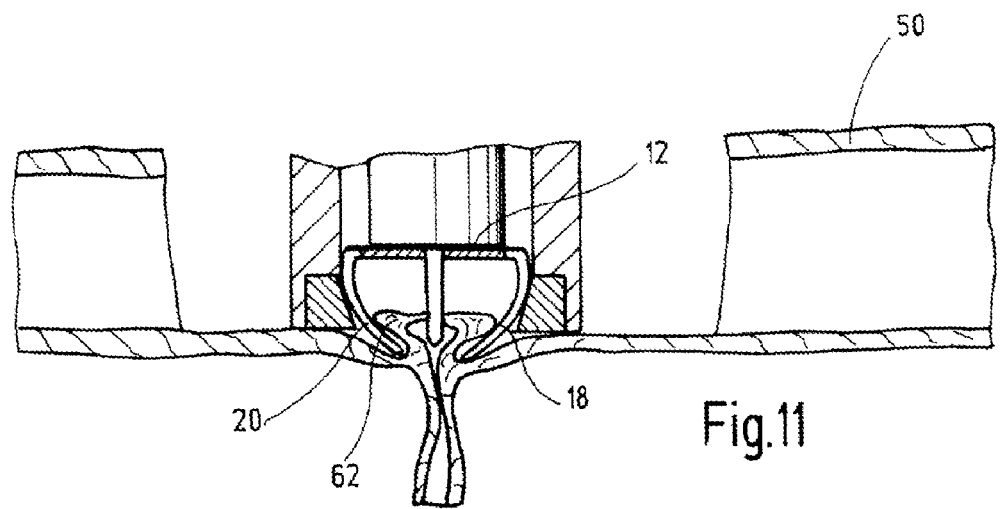
FIG. 11 shows a view corresponding to FIG. 6, with the bent-back limbs having already worked themselves into the tissue of the aorta.
Figure 12:
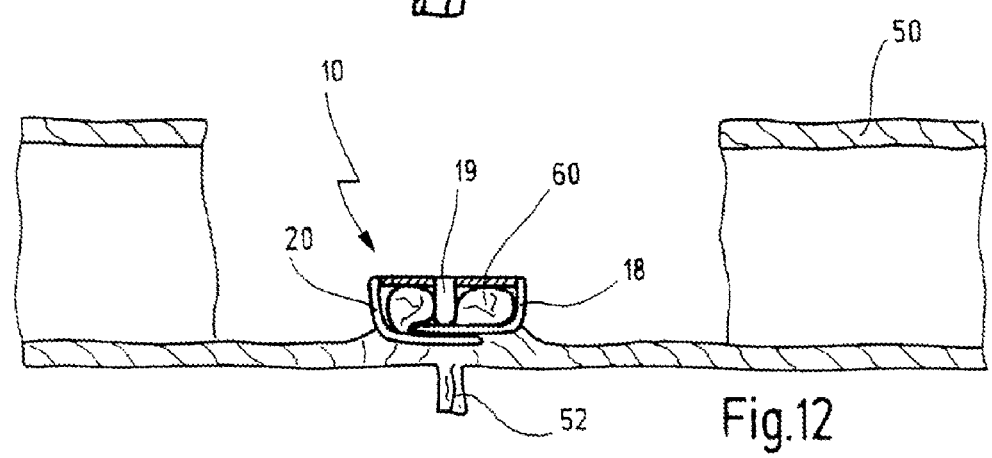
FIG. 12 shows a view corresponding to FIG. 7, after the clip has been applied by the clip applicator.
Figure 13:
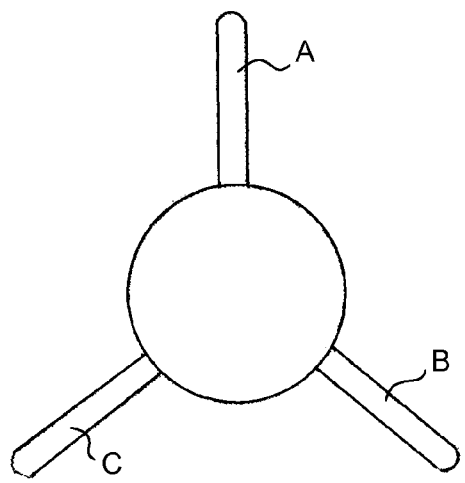
FIG. 13 shows a plan view of one embodiment of a clip of the present invention after the original production process, in which the base body and three limbs extend in one plane.
Figure 14:
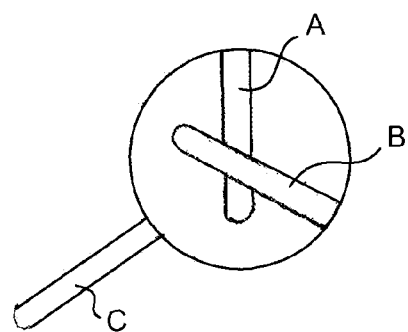
FIG. 14 shows a plan view of one embodiment of a clip of the present invention wherein a first limb A has been bent-back and a second limb B has been sequentially bent back over first limb A.
Figure 15:
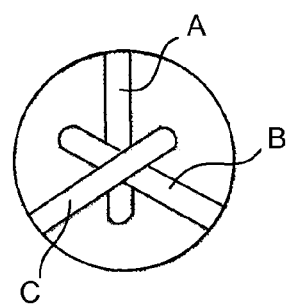
FIG. 15 shows a plan view of one embodiment of a clip of the present invention wherein a third limb C has been sequentially bent-back over second limb B, to form a cage-shape.

The sequence of figures from FIG. 10 to FIG. 12 shows how a clip 10 according to the invention is applied using a clip applicator 30 according to the invention. To do so, a main blood vessel 50, for example the aorta, is clamped off at two separate locations and is opened in this area by means of a lengthwise incision. By this means, it is then possible to bring the distal end 31 of the clip applicator 30 to the inside face 54 of the opened aorta 50 from one side, as is shown in FIG. 10. This is done in the area of a branch 56 where the other blood vessel 52, for example an artery, branches off from the main blood vessel 50. This means that an opening 58 exists in the wall of the main blood vessel 50, which opening 58 is to be closed.

The situation in FIG. 10 corresponds to the situation in FIG. 5. The transition from FIG. 10 to FIG. 11 corresponds to the transition from FIG. 5 to FIG. 6.

It will be seen from FIG. 11 that the curved ends of the limbs 18 and 20 advanced past the distal end 31 (the same of course also applying to the other three limbs 19, 21 and 22) have worked their way into the tissue 62 in the area around the opening 58 and, when further advanced, carry areas of the tissue 62 with them into the space between the base body 12 and the bending-back limbs. In this way, a kind of plug 60 of tissue 62 is formed which, in the same way as before, is connected via a mushroom-shaped neck to the inside face 54 of the main blood vessel 50 and is located in the space inside the bent-back clip 10. The opening 58, and consequently the blood vessel 52, is closed off by this plug 60. The undesired flow of blood can be ruled out in this way.

What is claimed is:

1. A clip applicator for applying a clip, said clip having a base body and at least three limbs protruding from said base body, said clip applicator having a housing for receiving at least one clip,
    an advancer mechanism for pushing a clip forwards, and
    a stationary deflector element for bending back said limbs of said clip having been pushed forwards and has struck said deflector element,
    said deflector element having oblique deflector surfaces on the inside of the applicator for deflecting said limbs of said clip radially inwards,
    wherein said deflector surfaces have different height levels at the clip entry point, so that the limbs can be bent back beginning one after another.

2. The clip applicator of claim 1, wherein said deflector element comprises an annular body having said radially inwardly sloping deflector surfaces recessed therein.

* * * * *